United States Patent [19]
Dziabo et al.

[11] Patent Number: 5,340,583
[45] Date of Patent: Aug. 23, 1994

[54] ANTIMICROBIAL LENSES AND LENS CARE SYSTEMS

[75] Inventors: Anthony J. Dziabo, Lake Forest; Alix A. Holmes, Costa Mesa; Claude B. Anger, Long Beach; John C. Baker, Irvine; Lin Peng, Tustin, all of Calif.

[73] Assignee: Allergan, Inc., Irvine, Calif.

[21] Appl. No.: 59,025

[22] Filed: May 6, 1993

[51] Int. Cl.5 .......................... A01N 25/34; G02C 7/04
[52] U.S. Cl. ...................................... 424/412; 424/409; 424/429; 514/839; 514/840
[58] Field of Search ............... 424/78.04, 409, 412, 424/429; 514/839, 840

[56] References Cited

U.S. PATENT DOCUMENTS

| | | | |
|---|---|---|---|
| 3,211,281 | 10/1965 | Speshyock | 424/429 |
| 3,279,996 | 10/1966 | Long, Jr. et al. | 424/424 |
| 3,591,329 | 7/1971 | Chromecek | 424/412 |
| 3,966,902 | 6/1976 | Chromocek | 206/5.1 |
| 4,442,125 | 4/1984 | Thiele | 424/412 |
| 4,817,998 | 4/1989 | Ryder et al. | 294/1.1 |
| 5,013,459 | 5/1991 | Gettings et al. | 210/764 |
| 5,059,402 | 10/1991 | Seamons et al. | 422/300 |

Primary Examiner—Thurman K. Page
Assistant Examiner—Carlos Azpuru
Attorney, Agent, or Firm—Frank J. Uxa

[57] ABSTRACT

The present invention relates to lenses, for example, contact lenses, and to contact lens cases having antimicrobial properties. More particularly, the invention relates to lenses and contact lens cases made from materials which comprise polymeric materials and effective antimicrobial components.

13 Claims, 1 Drawing Sheet

ANTIMICROBIAL LENSES AND LENS CARE SYSTEMS

BACKGROUND OF THE INVENTION

The present invention relates to lenses, for example, contact lenses, and to contact lens care systems, having antimicrobial properties. More particularly, the invention relates to lenses and contact lens containers or cases made from antimicrobial materials, for example, polymeric materials which include antimicrobial components.

Contact lenses are often exposed to one or more microorganisms which can result in detrimentally affecting the mammalian eye in which the lens is used. Conventional contact lenses should be periodically disinfected by the user to prevent infection or other deleterious effects on ocular health which may be associated with contact lens wear. For example, there are several different conventional systems and methods which enable the user to disinfect his/her contact lenses between wearing times.

Microbial, e.g., bacterial, contamination of contact lens containers or cases used for contact lens care products is a further significant problem. The contact lens case has been implicated as a factor in microbial keratitis due to the fact that most contact lens disinfection systems are designed to deal with contamination on the contact lens, and not necessarily with contamination existing in the contact lens case. Thus, a disinfected contact lens placed in a contaminated contact lens case may itself become contaminated prior to being placed in the eye. This at least partially negates the beneficial effects of contact lens disinfecting. Contact lens cases are continually exposed to environmental contaminants, as well as to the contact lenses themselves. Such contact lens cases often set up a biofilm which is nutritive and protective of microorganisms.

Chromecek et al U.S. Pat. No. 3,591,329 discloses storing and disinfecting hydrophilic gel contact lenses in a system to disinfect the lens consisting of a receptacle divided into two compartments separated by a permeable partition. In one compartment, the hydrophilic lens is stored under an aqueous liquid, while located in the other compartment is a water swellable polymer containing surface active silver ion exchanged onto the polymer. Silver ions from this polymer dissolve in the surrounding aqueous liquid and penetrate into the lens to kill budding spores on the lens. The silver ions released from the polymer have at least the potential of detrimentally affecting the contact lens in the compartment. Also, because the silver on the polymer is being continually depleted, the silver-containing polymer may be effective for only a relatively short period of time.

SUMMARY OF THE INVENTION

New lenses, for example, contact lenses, and lens care systems have been discovered. The present lenses and systems provide effective antimicrobial properties against one or more microorganisms to which a contact lens is exposed. Contact lenses having such antimicrobial properties have a reduced tendency to become contaminated and may, therefore, require less frequent disinfection procedures. In certain instances, the present lenses may not need to be separately disinfected in order to be effectively free of microbial contamination. For example, the present lenses may be stored at conditions which do not normally result in disinfection of the lens and, because of the antimicrobial properties of the lens, provide the lens in a disinfected or microbially uncontaminated state. The present lens cases also advantageously have antimicrobial properties which reduce not only contamination of these cases themselves, but also the lenses, e.g., contact lenses which are located, from time to time, in such cases. In this manner, the chances or probabilities of contaminating lenses are reduced, and may even be substantially eliminated.

Importantly, the presently useful antimicrobial components do not need to migrate into or through a liquid medium to provide the desired antimicrobial properties, and are, in fact, preferably substantially non-leachable, e.g., into the eye fluids or liquid media, under normal use conditions. Thus, the presently useful antimicrobial components preferably remain associated with the lens or lens case and are effective for relatively long periods of time, even indefinitely. The present invention, as will be discussed hereinafter, is relatively easy to practice, and results in substantial benefits, for example, to wearers of contact lenses.

In one broad aspect, the present invention is directed to a lens, preferably a corneal contact lens or simply a contact lens, structured to be used in a mammalian eye. This lens comprises a lens body, preferably an optically clear lens body, including a polymeric material and an effective amount of an antimicrobial component, preferably an antimicrobial component which is substantially non-leachable under normal use conditions of the lens, effective against at least one, preferably a plurality and more preferably substantially all, of the microorganisms to which the lens is exposed, for example, while inside and/or outside the eye. The antimicrobial component may be a component or part of the polymeric material or may be physically, chemically or otherwise combined with the polymeric material, for example, after the polymeric material is formed. The antimicrobial component may be present primarily (i.e., at least about 50% of the antimicrobial component), or even substantially wholly, at or near the external surface of the lens body, or may be substantially uniformly distributed throughout the lens body. In one embodiment, the antimicrobial component is substantially metal-free, for example, silver- free.

In a further broad aspect, the present invention is directed to a lens case, preferably a contact lens case, which comprises at least one container section, preferably two container sections, sized and adapted to define a space in which to hold a lens, preferably a contact lens, when the lens is not in use in the eye. This container section is made at least partially, and preferably substantially wholly, of a material comprising a polymeric material and an antimicrobial component, preferably an antimicrobial component which is substantially non-leachable under normal use conditions, effective against at least one, preferably a plurality and more preferably substantially all, of the microorganisms to which a lens, for example, a contact lens, is exposed, for example, while inside and/or outside the eye. Preferably, the container section is structured so that the contact lens held in the container section contacts the material making up the container section. In a particularly useful embodiment, the lens case is structured so that liquid, for example, a saline solution, can enter therein and contact the lens being held in the space defined by the container section. The antimicrobial component may be present primarily, or even substantially wholly, at or near the external surface of the container section, preferably an external surface which contacts the lens being held in the space defined by the container section, or may be substantially uniformly distributed throughout the container section. In one embodiment, the antimicrobial component is substantially metal-free, for example, silver- free.

The presently useful antimicrobial components are preferably substantially non-leachable. Thus, the presently useful antimicrobial component preferably is such that it does not migrate, for example, from the lens or the lens case with which it is originally associated, into a liquid contacting the antimicrobial component under normal use conditions. Such substantially non-leachable antimicrobial components do not contaminate fluids in the eye or liquids used to care for contact lenses under normal use conditions.

As used herein, the term "an amount effective against" as it relates to any particular microorganism means that the antimicrobial component to which this term is applied is present in the item with which such antimicrobial component is associated in an amount effective to reduce the microbial burden on the item by one log order in about 20 hours, preferably in about 15 hours, and more preferably in about 10 hours.

The present lenses and container sections preferably include a major amount of the polymeric material, more preferably at least about 90% by weight of the polymeric material. The antimicrobial component is preferably present in an amount of at least about 0.005% by weight and less than about 10% by weight, more preferably less than about 5% by weight and still more preferably less than about 1% by weight of lens body or container sections.

Although the present invention is described hereinafter in terms of a contact lens and contact lens case, it should be noted that the invention is also applicable to other types of lenses, such as intraocular lenses, corneal inlay and onlay lenses and the like, and to containers for such lenses. However, the invention is particularly applicable to contact lenses and to contact lens cases or containers.

These and other aspects of the present invention are set forth in the following detailed description and claims, particularly when considered in conjunction with the accompanying drawings in which like parts bear like reference numerals.

DETAILED DESCRIPTION OF THE INVENTION

Figure 1:
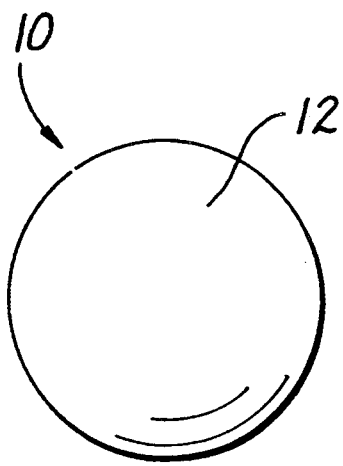
FIG. 1 is a top plan view of a contact lens in accordance with the present invention.
Figure 2:
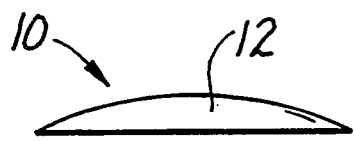
FIG. 2 is a side plan view of the contact lens shown in FIG. 1.

Referring now to the drawings, FIGS. 1 and 2 illustrate a contact lens 10 in accordance with the present invention. Contact lens 10 includes an optically clear contact lens body 12 and is useful as a conventional contact lens on the cornea of a human eye to correct the vision in such eye.

Contact lens body 12 is made of a material which includes a suitable polymeric material and an effective, substantially silver-free, substantially non-leachable antimicrobial component. The antimicrobial component is preferably covalently bonded to the polymeric material. This antimicrobial component is present in an amount effective against at least one, preferably a plurality and even substantially all of the microorganisms to which contact lens 10 is exposed.

In formulating the material for use in contact lens body 12, it is important that the material be optically clear, be suitable for use in the eye and be otherwise suitable as a contact lens material of construction. The antimicrobial component included in contact lens 10 should be ophthalmically acceptable. That is, such antimicrobial component should be selected so as to have, or to cause, no significant adverse effect on the wearer, in particular on the ocular health of the wearer, of the contact lens including this component.

The polymeric material useful in contact lens 10 may be substantially any such material useful as a component in corneal contact lenses, for example, conventional corneal contact lenses. This polymeric material may be synthetic, naturally occurring or a combination, e.g., mixture, of synthetic and naturally occurring polymers. Examples of polymeric materials which may be included in contact lens body 12 include silicone polymers, such as polysiloxanes and the like; polyolefins, such as polyethylene, polypropylene and the like; polyesters; polyurethanes; acrylic polymers, such as polyacrylates and polymethacrylates; hydrogel-forming polymers; polycarbonates and the like.

Contact lens 10 can be provided with a substantially non-leachable antimicrobial component in any suitable manner. In one embodiment, a pre-formed contact lens, that is a lens which is already formed, is contacted with an antimicrobial material at conditions effective to form a contact lens, such as contact lens 10, including an effective amount of the substantially non-leachable antimicrobial component, preferably covalently bonded to the polymeric material included in the body of the contact lens, such as contact lens body 12. In this embodiment, the antimicrobial component is preferably present primarily, and even substantially wholly, at or near an external surface, for example, all the external surfaces, of the body of the contact lens.

With regard to a system for contacting, e.g., treating, a pre-formed contact lens to provide an effective antimicrobial component, a reactable component is preferably employed. Such reactable components include an active (antimicrobially active) portion and a functional portion. Preferably, the active portion of the reactable component is covalently linked to the functional portion. The active portion of the reactable component is such is to provide the predominant, and even substantially the total, amount of antimicrobial activity to the antimicrobial component. Examples of useful active portions include antimicrobial quaternary ammonium-containing groups, antimicrobial amine-containing groups, antimicrobial peptide-containing groups, antimicrobial phosphazene-containing groups and the like and mixtures thereof. Antimicrobial quaternary ammonium-containing groups and mixtures thereof are particularly useful.

The functional portion of the reactable component is such as to interact, preferably chemically react, with the material of the pre-formed contact lens to bond, preferably chemically bond and more preferably covalently bond, the antimicrobial component to the contact lens. Thus, the functional portion is chosen so as to be reactable, preferably chemically reactable, with the material of the preformed contact lens. The specific functional portion selected, of course, depends on the specific pre-formed contact lens material being used. Examples of useful reactable component functional portions include organosilane groups, epoxide groups, aziridine groups, sulfhydryl groups, activated ester groups, rosylate groups, vinyl sulfone groups, and the like and mixtures thereof.

One very effective class of reactable components include quaternary ammonium-containing organosilanes, preferably quaternary ammonium-containing organosiloxanes. A particularly useful reactable component or antimicrobial material for use in providing contact lens 10 with an effective antimicrobial component is a quaternary ammonium-containing organosilane component selected from the group of compounds having one of the following structures or formulas:

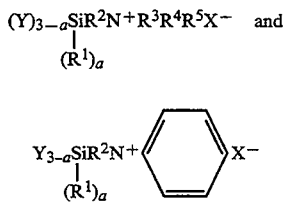

and mixtures thereof, wherein, in each formula,

Y is R or RO where each R is independently selected from alkyl radicals containing 1 to about 4 carbon atoms and hydrogen;
a has a value of 0, 1 or 2;
$R^1$ is a methyl or ethyl radical;
$R^2$ is an alkylene group of 1 to about 4 carbon atoms;
$R^3$, $R^4$ and $R^5$ are each independently selected from the group consisting of alkyl radicals of 1 to 18 carbon atoms, $-CH_2C_6H_5$, $-CH_2C_2OH$, $-CH_2OH$, and $-(CH_2)_xNHC(O)R^6$, wherein x has a value of from 2 to about 10 and $R^6$ is a perfluoroalkyl radical having from 1 to 12 carbon atoms; and
X is chloride, bromide, fluoride, iodide, acetate or tosylate.

Such antimicrobial components are more fully described in Gettings et al U.S. Pat. No. 5,013,459, which is incorporated in its entirety by reference herein.

For purposes of this invention, the silanes can be used neat or they can be used in solvent or aqueoussolvent solutions in contacting the presently useful polymeric materials, for example, a pre-formed contact lens including such a polymeric material. When the silanes are used neat, they are preferably used with a small amount of water. If it is not possible to have a small amount of water present, then a water soluble or water-dispersable, low molecular weight hydrolyzate of the silane may be used. What is important is the fact that the durability of any antimicrobial effect produced by the silane as part of the polymeric material, e.g., making up contact lens 10, requires that the silane molecule react with the polymeric material, in particular the polymeric material at or near the external surface of the pre-formed contact lens, to a certain extent. The most reactive species, as far as the silanes are concerned, is the $\equiv$SiOH that is formed by hydrolysis of the silane, for example, by hydrolysis of the alkoxy groups present on the silane. The $\equiv$SiOH groups tend to react with the polymeric material at or near the surface and to bind the silane moieties to the polymeric material at or near the surface. The alkoxy groups on the silicon atom may also participate in their own right to bind to the surface.

In one embodiment a reactive polymeric material surface containing a small amount of water is provided. By "reactive", is meant that the polymeric material surface contains some groups which react with one or more of the groups, e.g., silanols generated by hydrolysis of the silanes.

The R groups in the silanes are alkyl groups of 1 to about 4 carbon atoms. Thus, useful as R include methyl, ethyl, propyl and butyl radicals. In the above formulas, RO can also be R. R can also be hydrogen, thus indicating the silanol form, a hydrolyzed form. The value of a is 0, 1 or 2, and $R^1$ is a methyl or ethyl radical. Because of the presence of these alkyl radicals, the silanes should be stabilized with a corresponding solvent. Thus, methoxy groups require methanol and ethoxy groups require ethanol, for example.

The $R^2$ group is an alkylene group of 1 to 4 carbon atoms. Thus, $R^2$ can be alkylene groups such as methylene ethylene propylene and butylene. The $R^3$, $R^4$, and $R^5$ groups are each independently selected from a group which consists of alkyl radicals of 1 to 18 carbons, $-CH_2C_6H_5$, $-CH_2CH_2OH$, $-CH_2OH$, and $-(CH_2)_xNHC(O)R^6$, x has a value of from 2 to about 10 and $R^6$ is a perfluoroalkyl radical having from 1 to 12 carbon atoms. X is chloride, bromide, fluoride, iodide, acetate or tosylate.

Preferred for this invention are the silanes of the general formula

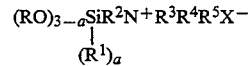

wherein R is methyl or ethyl; a has a value of zero; $R^2$ is propylene; $R^3$ is methyl or ethyl; $R^4$ and $R^5$ are selected from alkyl groups containing 1 to about 18 carbon atoms wherein at least one such group is larger that eight carbon atoms and X is either chloride, acetate or tosylate.

Specific silanes useful in the invention are represented by the formulae:

$(CH_3O)_3Si(CH_2)_3N^+(CH_3)_2CH_{18}H_{37}Cl^-$,
$(CH_3O)_3Si(CH_2)_3N^+(CH_3)_2CH_{18}H_{37}Br^-$,
$(CH_3O)_3Si(CH_2)_3N^+(C_{10}H_{21})_2CH_3Cl^-$,
$(CH_3O)_3Si(CH_2)_3N^+(C_{10}H_{21})_2CH_3Br^-$,
$(CH_3O)_3Si(CH_2)_3N^+(CH_3)_3Cl^-$,
$(CH_3O)_3SiCH_2CH_2CH_2N^+(C_6H_5)_3Cl^-$,
$(CH_3O)_3SiCH_2CH_2CH_2N^+(C_6H_5)_3Br^-$,
$(CH_3O)_3SiCH_2CH_2CH_2N^+(CH_3)_3Cl^-$,
$(CH_3O)_3SiCH_2CH_2CH_2N^+(C_6H_{13})_3Cl^-$,
$(CH_3)_3SiCH_2)_3N^+(CH_3)_2C_{12}H_{25}Cl^-$,
$(CH_3)_3SiCH_2)_3N^+(C_{10}H_{21})_2CH_3Cl^-$,
$(CH_3)_3SiCH_2)_3N^+(CH_3)_2C_{18}H_{37}Cl^-$,
$(CH_2O)_3Si(CH_2)_3N^+(CH_3)_2C_4H_9Cl^-$,
$(CH_3O)_3Si(CH_2)_3N^+(CH_3)_2CH_2C_6H_5Cl^-$,
$(CH_3O)_3Si(CH_2)_3N^+(CH_3)_2CH_2OHCl^-$,

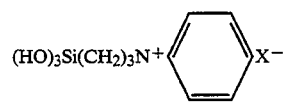

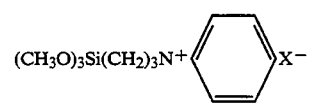

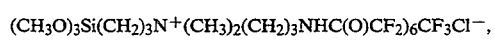

$(CH_3O)_3Si(CH_2)_3N^+(CH_3)_2(CH_2)_3NHC(O)CF_2)_6CF_3Cl^-$,

-continued $(CH_3O)_3Si(CH_2)_3N^+(CH_2H_5)_3Cl^-$.

In another embodiment, a contact lens body, such as contact lens body 12, is made by polymerizing one or more monomers chosen to provide the polymeric material and the antimicrobial component. In this manner, the resulting polymer or copolymer has a substantially nonleachable, covalently bonded antimicrobial component inherent in the polymer structure. The antimicrobial component is preferably substantially uniformly distributed throughout the polymer or copolymer. The polymer or copolymer can then be formed into a contact lens, such as contact lens 10. Of course, in the event a copolymer is employed, the monomer from which the antimicrobial component is derived should be chosen to be compatible (for example, reactable) with one or more of the other monomers employed and so as to provide a copolymer with the desired combination of properties from which a contact lens, such as contact lens 10, can be formed. The polymer or copolymer should be optically clear and otherwise useful as a contact lens material. In addition, the polymer or copolymer should include an antimicrobial component (derived from the antimicrobial monomer or monomers used to produce the polymer or copolymer) in an amount effective against at least one, preferably a plurality and even substantially all, of the microorganisms to which contact lens 10 is exposed. One particularly useful class of antimicrobial components for inclusion in contact lens 10 are those antimicrobial components derived from antimicrobial protonated amine-containing materials (preferably monomers), antimicrobial polypeptide-forming materials (preferably monomers), antimicrobial polyphosphazene-forming materials (monomers), and the like and mixtures thereof.

For example, particularly when the polymeric material is acrylic in nature, the antimicrobial component may be derived from the copolymerization of one or more acrylic monomers and an acrylic protonated amine comonomer and/or by including protonated amine end groups in the polymeric material. In any event, the protonated amine sites (which may be considered the "antimicrobial component") are part of the polymer chain, that is such sites are covalently bonded to the polymer chain and preferably are substantially uniformly distributed throughout the polymer. Such materials and their methods of preparation are more fully described in Pardini U.S. Pat. No. 4,708,870, which is incorporated in its entirety by reference herein.

A suitable material for use in the present invention is a copolymer of (1) acrylonitrile, (2) one or more neutral vinyl monomers and (3) a protonated amine monomer. Examples of amine monomers from which the protonated amine antimicrobial component can be derived include diethylaminoethyl methacrylate, 2-methyl-5-vinylpyridine, dimethylaminopropylmethacryloamide and the like.

The contact lens 10 made from the above-noted copolymers can be formed while the monomer mixture is being polymerized or from the copolymer, for example, using conventional contact lens forming techniques.

Once contact lens 10 is formed, it has sufficient antimicrobial activity to at least prolong the time between separate disinfections of the lens. This feature at least reduces the need to separately disinfect contact lens 10 and, therefore, reduces the amount of care that a contact lens wearer needs to take without detrimentally affecting or risking his or her ocular health.

In one embodiment, the contact lens 10 has sufficient antimicrobial activity so that no separate disinfection procedure of the lens is required. In this embodiment, contact lens 10 can be stored in a preserved contact lens soaking solution, such as is commercially available, while the lens is not in use in the eye. Such soaking is satisfactory to maintain contact lens 10 suitably free of microorganisms without the need for a separate disinfection procedure, for example, contacting contact lens 10 with hydrogen peroxide.

Contact lens 10 can include other components, such as UV light absorbers, dyes and the like, which are conventionally present in contact lenses in an amount effective to provide one or more desired properties to the lens.

Figure 3:
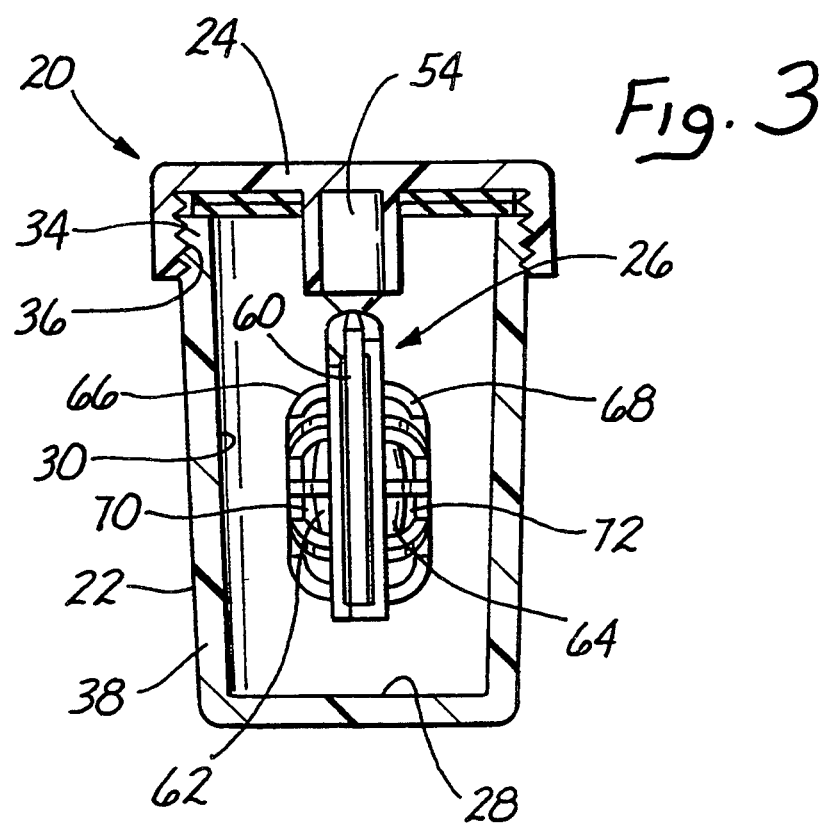
FIG. 3 is a side view, partially in cross section, showing one embodiment of a contact lens case in accordance with the present invention.

Referring now to FIG. 3, a contact lens case, shown generally at 20, includes lens container 12, a cover 24 and a lens basket 26.

Lens container 22 is made of a transparent, thermoplastic polymeric material, such as polymethylmethacrylate and the like, and is made, e.g., molded, using conventional techniques as a single unit. Lens container 22 includes a bottom wall 28 and a sidewall 30. Top 34 of sidewall 30 includes a threaded outer surface 36. The cross section of lens container 22 parallel to bottom wall 28 is generally circular. Lens container 22 defines an interior space 38 in which is placed a conventional contact lens soaking composition, e.g., a preserved saline solution.

Lens basket 26 is made of a non-transparent material including a polymeric material and a substantially non-leachable antimicrobial component. The polymeric material useful in lens basket 26 may be substantially any such material useful as a component in such contact lens holders, for example, in conventional contact lens cases. Examples of polymeric materials from which lens basket 26 can be made include polyolefins, such as polyethylene, polypropylene and the like; polyesters; polyurethanes; acrylic polymers, such as polyacrylates and polymethacrylates; polycarbonates and the like.

The antimicrobial component included in lens basket 26 can be derived from the antimicrobial materials as described previously with regard to contact lens 10. This antimicrobial component is present in an amount effective against at least one, preferably a plurality and even substantially all, of the microorganisms to which the contact lenses held in the space defined by lens basket 26 are exposed.

Although the antimicrobial component may be substantially metal-free, for example, silver-free, in one useful embodiment a substantially non-leachable, metal-containing antimicrobial component is employed. Such metal components include, for example, silver components, copper components and other antimicrobial metal components. Silver components are especially useful for inclusion in lens basket 26 as antimicrobial components. Such metal components have antimicrobial activity substantially without being leached into the surrounding liquid medium. That is, for example, the antimicrobial activity of lens basket 26 including such a metal component is increased beyond the antimicrobial activity caused by any metal ions leached into the liquid medium. This is in contrast to the system of Chromecek et al U.S. Pat. No. 3,591,329 in which silver ions are continually released (leached) from the polymer to provide the antimicrobial effect. The present lens basket 26 including an appropriate substantially non-leachable antimicrobial metal component remains antimicrobially active and effective for a long, even indefinite, period of time in use.

Lens basket 26 can be provided with a substantially non-leachable antimicrobial component in any suitable manner, for example, in ways which are analogous to those previously described with regard to providing contact lens 10 with such an antimicrobial component. Thus, a pre-formed lens basket (or pre-formed components of a lens basket) can be contacted with a suitable antimicrobial material to provide an effective antimicrobial component, for example, primarily at or near the external surface or surfaces of the lens basket (or component thereof). A very useful method of providing the pre-formed lens basket with an antimicrobial metal component is to subject the pre-formed lens basket to one or more metal deposition techniques, for example, metal ion beam assisted deposition. Alternately, the lens basket 26 (or components of the lens basket) can be formed of a copolymer derived from monomers including one or more antimicrobial monomer. In this embodiment, the antimicrobial component is preferably substantially uniformly distributed throughout the lens basket 26 (or components of the lens basket).

Like lens container 22 and cover 24, lens basket 26 can be made, e.g., molded, using conventional techniques. Lens basket 26 includes attachment element 54 which is secured to cover 24 extending downwardly from attachment element 54 is basket body 60 which includes left lens mount 62 and right lens mount 64. Basket body 60 includes a series of through holes which allow liquid to freely pass through the basket body.

A left basket cover 66 and a right basket cover 68 are both hingedly secured to basket body 60 and are structured to be "snapped" closed around left lens mount 62 and right lens mount 64, respectively, as desired, to form a left lens compartment 70 and a right lens compartment 72, respectively. The basket covers 66 and 68 are made separately from the other components of the lens basket 26. Each of the basket covers 66 and 68 includes a series of through holes which allow liquid to flow freely through. However, these through holes are sized so that the contact lenses in lens compartments 70 and 72 cannot be removed when the lens covers 66 and 68 are closed. Left lens covered may be marked with "L" to indicate that it is to be used with the left contact lens. Similarly, the right lens cover 68 may be marked with a "R" to indicate that it is to be used with a right contact lens. The contact lens positioned in each of the lens compartments 60 and 62 contact at least one point of the lens basket 26. Thus, such contact lens held in each of the lens compartments 66 and 68 are in contact with a material including an effective antimicrobial component.

Lens container apparatus 20 may be used as follows: with cover 24 removed from lens container 22, the contact lenses, after having been used in the eye and disinfected are placed on the appropriate left and right lens mounts 62 and 64, respectively, and the left and right lens basket covers 66 and 68 are snapped closed. A quantity, e.g., about 10 ml, of a conventional preserved aqueous saline solution is placed in the interior space of lens container 22. In this manner, the contact lenses held in lens basket 26 are maintained in the disinfected condition, even though they may be stored for a prolonged period of time.

When it is desired to use the contact lenses being held in lens basket 26, they may be removed from lens basket 26 by simply unsnapping the basket covers 66 and 68, and removing the lenses. The removed lenses can be placed directly in the eye for safe and comfortable wear.

While this invention has been described with respect to various specific examples and embodiments, it is to be understood that the invention is not limited thereto and that it can be variously practiced within the scope of the following claims.

What is claimed is:

1. A contact lens case comprising at least one container section sized and adapted to define a space in which to hold a contact lens when the contact lens is not in use, said at least one container section being made at least partially of a material comprising a polymeric material and an antimicrobial component which is non-leachable under normal use conditions and is present in an amount effective against one or more microorganisms to which a contact lens is exposed.

2. The contact lens case of claim 1 wherein said at least one container section includes one or more contact portions which normally contact the contact lens held in said at least one container section, said one or more contact portions including said material.

3. The contact lens case of claim 1 which includes two of said container sections each of which is adapted to hold a single contact lens when the contact lens is not in use.

4. The contact lens case of claim 1 wherein said at least one container section is structured so that liquid can enter therein and contact said contact lens being held in said at least one container section.

5. The contact lens case of claim 1 wherein said antimicrobial component is covalently bonded to said polymeric material.

6. The contact lens case of claim 1 wherein said at least one container section includes a major amount of said polymeric material and at least about 0.005% by weight of said antimicrobial component.

7. The contact lens case of claim 1 wherein said at least one container section include less than about 10% by weight of said antimicrobial component.

8. The contact lens case of claim 1 wherein said antimicrobial component is derived from the group consisting of antimicrobial quaternary ammonium containing groups, antimicrobial amine-containing groups, antimicrobial peptide-containing groups, antimicrobial phosphazene-containing groups and mixtures thereof.

9. The contact lens care case of claim 1 wherein said antimicrobial component is a metal component.

10. The contact lens case of claim 1 wherein said antimicrobial component is a silver component.

11. The contact lens case of claim 1 wherein said antimicrobial component is present primarily at or near an external surface of said at least one container section.

12. The contact lens case of claim 1 wherein said antimicrobial component is uniformly distributed throughout said container section.

13. A contact lens case comprising at least one container section sized and adapted to define a space in which to hold a contact lens when the contact lens is not in use, said at least one container section being made-at least partially of a material comprising a polymeric material and an antimicrobial component which is silver-free and is present in an amount effective against one or more microorganisms to which a contact lens is exposed.

* * * * *

UNITED STATES PATENT AND TRADEMARK OFFICE
CERTIFICATE OF CORRECTION

PATENT NO. : 5,340,583
DATED : August 23, 1994
INVENTOR(S) : Dziabo et al.

It is certified that error appears in the above-indentified patent and that said Letters Patent is hereby corrected as shown below:

Column 4, line 54; delete "is" and insert in place thereof --as--.

Column 5, line 7; delete "rosy-" and insert in place thereof --tosy---.

Column 5, line 48; delete "aqueoussolvent" and insert in place thereof --aqueous-solvent--.

Column 6, line 21; insert a comma after each of --lene-- and --ethylene-- and --propylene--.

Column 9, line 45; delete "covered" and insert in place thereof --cover--.

Column 10, line 41, claim 7; delete "include" and insert in place thereof --includes--.

Signed and Sealed this

Fourth Day of April, 1995

Attest:

BRUCE LEHMAN

*Attesting Officer*     *Commissioner of Patents and Trademarks*